(12) United States Patent
Sugar et al.

(10) Patent No.: US 12,076,135 B2
(45) Date of Patent: Sep. 3, 2024

(54) SOFT HIP EXTENSION DEVICE TO AID HEMIPARETIC GAIT

(71) Applicants: Arizona Board of Regents on behalf of Arizona State University, Scottsdale, AZ (US); Dignity Health, San Francisco, CA (US)

(72) Inventors: Thomas Sugar, Chandler, AZ (US); Abhishu Patel, Tempe, AZ (US); Ryan Borneman, Laveen, AZ (US); Omik Save, Tempe, AZ (US); Yashaswy Govada, Tempe, AZ (US); Saivimal Sridar, Mesa, AZ (US); Pham Huy Nguyen, Mesa, AZ (US); Ammon Lovell, Phoenix, AZ (US)

(73) Assignees: Arizona Board of Regents on behalf of Arizona State University, Scottsdale, AZ (US); Dignity Health, San Francisco, CA (US)

( * ) Notice: Subject to any disclaimer, the term of this patent is extended or adjusted under 35 U.S.C. 154(b) by 34 days.

(21) Appl. No.: 16/859,597

(22) Filed: Apr. 27, 2020

(65) Prior Publication Data
US 2020/0337597 A1   Oct. 29, 2020

Related U.S. Application Data

(60) Provisional application No. 62/838,840, filed on Apr. 25, 2019.

(51) Int. Cl.
*A61H 3/00* (2006.01)
*A61B 5/11* (2006.01)
*A61F 5/01* (2006.01)

(52) U.S. Cl.
CPC .............. *A61B 5/112* (2013.01); *A61F 5/012* (2013.01); *A61H 2201/1628* (2013.01);
(Continued)

(58) Field of Classification Search
CPC .............. A61F 5/012; A61H 2201/165; A61H 2201/1628; A61H 3/00; A61H 2201/5071;
(Continued)

(56) References Cited

U.S. PATENT DOCUMENTS 4,422,449 A * 12/1983 Hamabe ................. A61H 15/00
                                                              601/102
7,048,707 B2 * 5/2006 Schwenn .............. A61F 5/0193
                                                              602/19
(Continued)

FOREIGN PATENT DOCUMENTS

EP        3342390 A1 * 7/2018 ............. A61H 1/024
WO     2004096083 A2    11/2004
(Continued)

OTHER PUBLICATIONS

S. Sridar, P. H. Nguyen, M. Zhu, Q. P. Lam and P. Polygerinos, "Development of a soft-inflatable exosuit for knee rehabilitation," 2017 IEEE/RSJ International Conference on Intelligent Robots and Systems (IROS), Vancouver, BC, 2017, pp. 3722-3727.
(Continued)

*Primary Examiner* — Michael R Reid
*Assistant Examiner* — Tyler A Raubenstraw
(74) *Attorney, Agent, or Firm* — Snell & Wilmer L.L.P.

(57) ABSTRACT

Disclosed herein are various embodiments of a soft robotic device for assisting hemiparetic patients. In embodiments, the soft robotic device includes an inflatable actuator capable of assisting hemiparetic patients with their gait cycle via application of a force on the gluteus muscle.

16 Claims, 16 Drawing Sheets

(52) U.S. Cl.
CPC .. *A61H 2201/164* (2013.01); *A61H 2201/165* (2013.01); *A61H 2201/5061* (2013.01); *A61H 2201/5071* (2013.01)

(58) Field of Classification Search
CPC ........... A61H 9/0078; A61H 2201/164; A61H 2201/5061; B25J 9/0006; A61B 5/112; A61B 5/103
See application file for complete search history.

(56) References Cited

U.S. PATENT DOCUMENTS

| | | | |
|---|---|---|---|
| 7,125,388 B1 | 10/2006 | Reinkensmeyer et al. | |
| 7,399,258 B1 | 7/2008 | Sugar et al. | |
| 9,192,487 B2 | 11/2015 | Flaven et al. | |
| 9,308,642 B2 | 4/2016 | Sugar et al. | |
| 10,548,800 B1* | 2/2020 | Barnes | A61H 1/0244 |
| 11,006,690 B2* | 5/2021 | Giedwoyn | G16H 40/63 |
| 2008/0319359 A1* | 12/2008 | Moomiaie-Qajar | A61H 11/00 601/152 |
| 2009/0248211 A1* | 10/2009 | Momose | G05D 7/0641 700/282 |
| 2009/0319054 A1* | 12/2009 | Sankai | A61F 5/0102 623/25 |
| 2011/0230806 A1* | 9/2011 | Lou | A61F 5/022 602/13 |
| 2013/0085429 A1* | 4/2013 | Nelsen | A61H 9/0078 601/149 |
| 2014/0213951 A1 | 7/2014 | Pietrusisnki et al. | |
| 2014/0277739 A1* | 9/2014 | Kornbluh | F16D 28/00 29/428 |
| 2017/0071816 A1* | 3/2017 | Vain | A61F 5/32 |
| 2017/0128237 A1* | 5/2017 | Rouse | A61F 5/012 |
| 2017/0181917 A1* | 6/2017 | Ohta | A61H 1/0281 |
| 2017/0189221 A1* | 7/2017 | Fullerton | A43B 7/38 |
| 2017/0216075 A1* | 8/2017 | Matsuzaki | A61F 5/0125 |
| 2017/0231792 A1* | 8/2017 | MacArthur | A61F 5/05866 602/13 |
| 2017/0246740 A1* | 8/2017 | Barnes | B25J 19/0016 |
| 2018/0079071 A1* | 3/2018 | Griffith | A61H 1/0244 |
| 2018/0221237 A1* | 8/2018 | Swift | G16H 50/20 |
| 2019/0015233 A1* | 1/2019 | Galloway | B25J 15/12 |
| 2019/0029914 A1* | 1/2019 | Polygerinos | A63B 23/0494 |
| 2019/0060157 A1* | 2/2019 | Lamb | A61H 1/0266 |
| 2019/0133871 A1* | 5/2019 | Chase | A41D 13/0015 |
| 2019/0283237 A1* | 9/2019 | Witherspoon | A61H 1/0237 |
| 2019/0336315 A1* | 11/2019 | Polygerinos | A61H 1/0266 |
| 2020/0093679 A1* | 3/2020 | Sonar | G01L 5/228 |
| 2020/0337931 A1 | 10/2020 | Shuch et al. | |
| 2020/0337933 A1 | 10/2020 | Sugar et al. | |
| 2020/0337937 A1 | 10/2020 | Sugar et al. | |

FOREIGN PATENT DOCUMENTS

| | | | | |
|---|---|---|---|---|
| WO | 2004096905 A2 | 11/2004 | | |
| WO | 2013086035 A1 | 6/2013 | | |
| WO | WO-2014194257 A1 * | 12/2014 | ............ | A61B 5/112 |
| WO | 2018017436 A1 | 1/2018 | | |
| WO | 2018122106 A1 | 7/2018 | | |
| WO | WO-2018207108 A1 * | 11/2018 | ........... | A61H 1/0244 |

OTHER PUBLICATIONS

C. M. Thalman, Q. P. Lam, P. H. Nguyen, S. Sridar and P. Polygerinos, "A Novel Soft Elbow Exosuit to Supplement Bicep Lifting Capacity," 2018 IEEE/RSJ International Conference on Intelligent Robots and Systems (IROS), Madrid, 2018, pp. 6965-6971.

J. Kim et al., "Autonomous and Portable Soft Exosuit for Hip Extension Assistance with Online Walking and Running Detection Algorithm," 2018 IEEE International Conference on Robotics and Automation (ICRA), Brisbane, QLD, 2018, pp. 5473-5480.

* cited by examiner

SOFT HIP EXTENSION DEVICE TO AID HEMIPARETIC GAIT

CROSS-REFERENCE TO RELATED APPLICATIONS

This application is a non-provisional patent application of, and claims priority to, U.S. Provisional Pat. App. No. 62/838,840 filed Apr. 25, 2019 and entitled "Soft Hip Extension Device to Aid Hemiparetic Gait," which is incorporated herein by reference in its entirety (except for any subject matter disclaimers or disavowals, and except to the extent of any conflict with the disclosure of the present application, in which case the disclosure of the present application shall control).

TECHNICAL FIELD

The present disclosure relates soft robotic systems, and in particular to systems for use in connection with gait assistance and/or training.

SUMMARY

In an aspect, a soft wearable robotic device is provided, comprising: an inflatable actuator configured for insertion inside a compressive hip brace; and control components configured to activate the inflatable actuator to provide a perpendicular force on the gluteus muscle groups responsive to a detection that the wearer is loading on an affected limb.

In embodiments, the control components comprise two interconnected solenoid valves and a pressure sensor. In embodiments, the soft wearable device further comprises a force-sensitive resistor (FSR) sensor configured to detect changes in force applied to the wearer's affected limb and figured to communicate the detected changes in force to the two interconnected solenoid valves.

In an aspect, device is provided, comprising: a hip brace comprising a pelvic strap and a thigh strap, wherein the hip brace covers one half of the pelvic region; and an inflatable fabric actuator comprising a pressurized air inlet, wherein the inflatable fabric actuator is attached to the pelvic strap and the thigh strap.

In embodiments, the device further comprises a force-sensitive resistor (FSR) sensor that is capable of being embedded in a shoe. In embodiments, the hip brace further comprises a lever arm. In embodiments, the lever arm is 0.04 meters. In embodiments, the inflatable fabric actuator comprises an area of no more than 0.0225 square meters, when the inflatable fabric actuator is not inflated. In embodiments, the inflatable fabric actuator comprises an area of contact on the pelvic strap of no more than 0.0025 square meters, when the inflatable fabric actuator is inflated. In embodiments, the inflatable fabric actuator is coated with thermoplastic polyurethane. In embodiments, the inflatable fabric actuator further comprises two interconnected solenoid valves and a pressure sensor, wherein the two interconnected solenoid valves and the pressure sensor are configured to control inflation and deflation of the inflatable fabric actuator. In embodiments, the device further comprises a compressor configured to pressurize the inflatable fabric actuator.

In an aspect, a system is provided comprising: an inflatable fabric actuator configured to be placed at a pelvis area of a patient, wherein, when inflated, the inflatable fabric actuator is capable of applying force behind a leg of the patient resulting in extension of a hip and straightening of the body.

In embodiments, the system further comprises a hip brace comprising: a first strap configured to secure the inflatable fabric actuator against the pelvis of the patient; and a second strap configured to secure the inflatable fabric actuator against the leg of the patient. In embodiments, the system further comprises a force-sensitive resistor (FSR) sensor configured to detect a load being applied to the leg and to communicate the detected load to the inflatable fabric actuator resulting in pressure changes in the inflatable fabric actuator causing deflation or inflation of the inflatable fabric actuator. In embodiments, the pressure changes in the inflatable fabric actuator comprise pressurizing the inflatable fabric actuator during mid-stance of a gait cycle resulting in straightening of the trunk of the patient.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting. The contents of this section are intended as a simplified introduction to the disclosure, and are not intended to limit the scope of any claim.

BRIEF DESCRIPTION OF THE DRAWINGS

With reference to the following description and accompanying drawings:

FIG. 4A depicts an actuator exerting force at full extension. FIG. 4B depicts an actuator exerting force at restricted extension.

FIG. 10A shows data when the device is not installed. FIG. 10B shows data when the device is installed. In both FIGS. 10A and 10B, the data representing the

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques and components may not be described in detail herein. Furthermore, the connecting lines shown in various figures contained herein are intended to represent exemplary functional relationships and/or physical couplings between various elements. It should be noted that many alternative or additional functional relationships or physical connections may be present in exemplary systems and/or components thereof.

Figure 1:
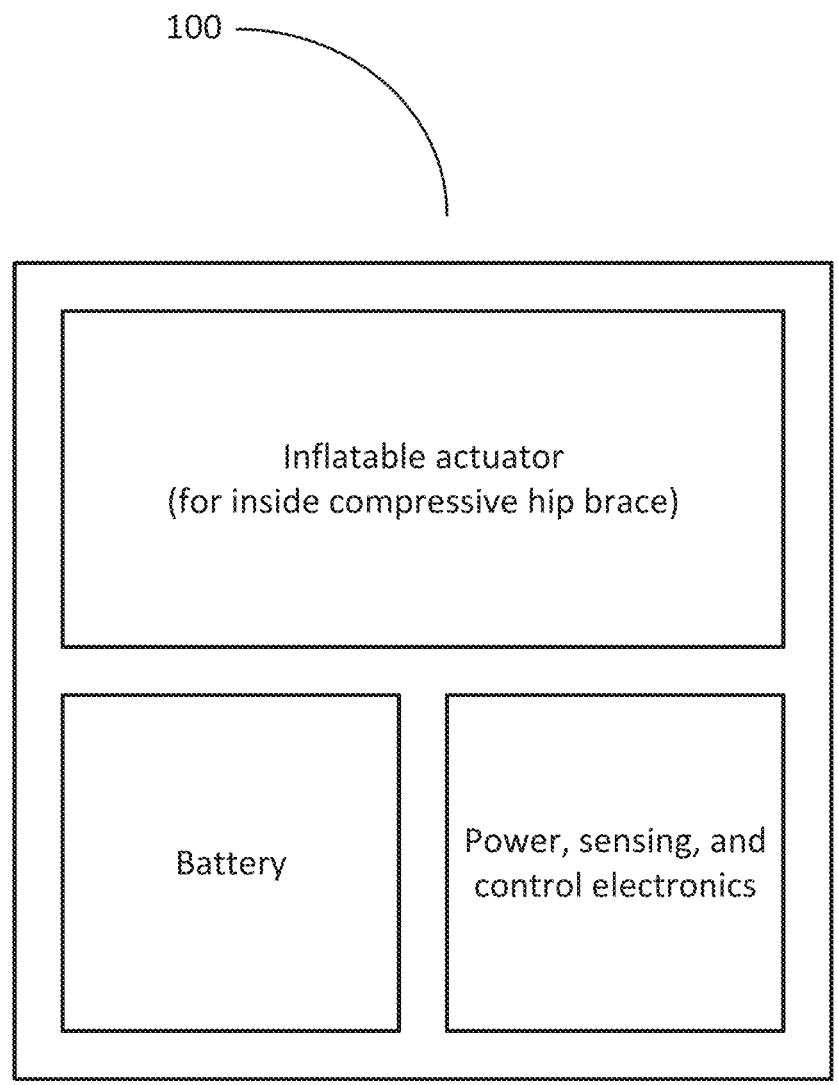
FIG. 1 illustrates an exemplary system in accordance with various exemplary embodiments.

With reference now to FIG. 1, in accordance with an exemplary embodiment, disclosed herein is a soft wearable device 100 for the hip which can induce a hip extension moment to the affected leg of the stroke patients to maintain a symmetric gait at walking speed, and also improve postural stability while walking. This device 100 uses heat sealable soft inflatable actuators to push the upper leg and assist the hip joint during walking so that the upper body does not fall forward during walking, improving postural stability. This soft hip extension device 100 may be utilized, for example, to assist a therapist to apply an extension moment if needed during physical therapy, or may be used as a standalone assistance platform for the user when incorporated with an insole.

Hemiparesis is a condition that affects about 8 out of 10 stroke survivors, causing weakness or the inability to move one side of the body. Patients who have this condition suffer from symptoms such as a loss of balance, the inability to walk or grasp objects properly, a decrease in movement precision, muscle fatigue and lack of coordination. Currently, there exist many solutions that assist patients with hemiparesis and other motor performance issues with the hips, such as the ALEX series exoskeletons, hip flexion assist devices, and soft exosuits. Most of the existing solutions for lower-limb assistance focus on bilateral applications to the leg, whereas those that focus on hemiparetic patients operate unilaterally, but with universal application for either leg. Patients with hemiparesis tend to lean forward as they are loading onto their affected leg. The patient does this because their bodies are attempting to place more weight on the weakened leg in an attempt to find support. When a patient leans forward, however, they perceive the support of their affected leg as weak, and this triggers them to reduce the movement of their healthy leg to a short step in order to anchor and stabilize themselves. This behavior affects the patient's ability to rehabilitate their affected limb and reduces the overall performance of their gait cycle.

Exemplary systems and principles herein can assist hemiparetic patients with their gait cycle by providing a more secure support to their affected leg via extension of their hips and providing postural stability. To address the problem, in various exemplary embodiments a soft robotic device 100, which applies a distributed load in the sagittal plane on the gluteus muscle groups is utilized. Device 100 may be utilized to replace the direct application of force a clinician currently uses to provide support to his/her patients as they undergo gait training. As such, a soft, comfortable device that conforms to the user's body, and operates using the sensing and actuating technologies in soft robotics is implemented. The device is designed to be inserted inside of a compressive hip brace and inflate to provide a perpendicular force on the gluteus muscle groups to propel the hips of the patient forward as the sensors detect the patient is loading on their affected limb. It also helps to straighten the body providing postural stability. In doing this, the exemplary device helps prevent the trunk of the user from tipping forward and the user shall experience an increased level of weight bearing on their affected limb, allowing them to carry out their gait training unimpaired.

In various exemplary embodiments, a hip extension device utilizing a soft-inflatable actuator that is to be attached to the affected hip of a stroke patient with the help of a hip brace and assists in propelling the hip forward. The device utilizes insole sensors to detect the walking pattern of the user. The actuator generates a pushing force to bring the patient's hip under their feet, preventing forward tipping whenever they put their affected foot down during walking. This then helps the patient to walk in a more symmetric gait cycle.

Previous devices used to treat hip extension used a pulling motion to extend the hip as in the case of wearable exosuits. In contrast, exemplary embodiments herein utilize a soft robotic actuator that generates a push motion on the hip muscle group. There have been previous approaches on generating a push motion to the pelvis, but have only been attempted using rigid exoskeletal systems.

In various exemplary embodiments, an inflatable fabric actuator is placed at the pelvis area that crossed the hip joint. When the actuator is inflated, it helps to straighten the trunk and tilt the trunk upward as well as assisting and extending the thigh.

In one exemplary embodiment, one strap of the system 100 was affixed around waist and held one side of the fabric actuator against the pelvis. A second strap was affixed around the thigh and held one side of the fabric actuator against the leg. The inflatable actuator consisted of a plastic pouch inside of fabric second layer. However, any suitable straps and actuators may be utilized, as desired.

Figure 2:
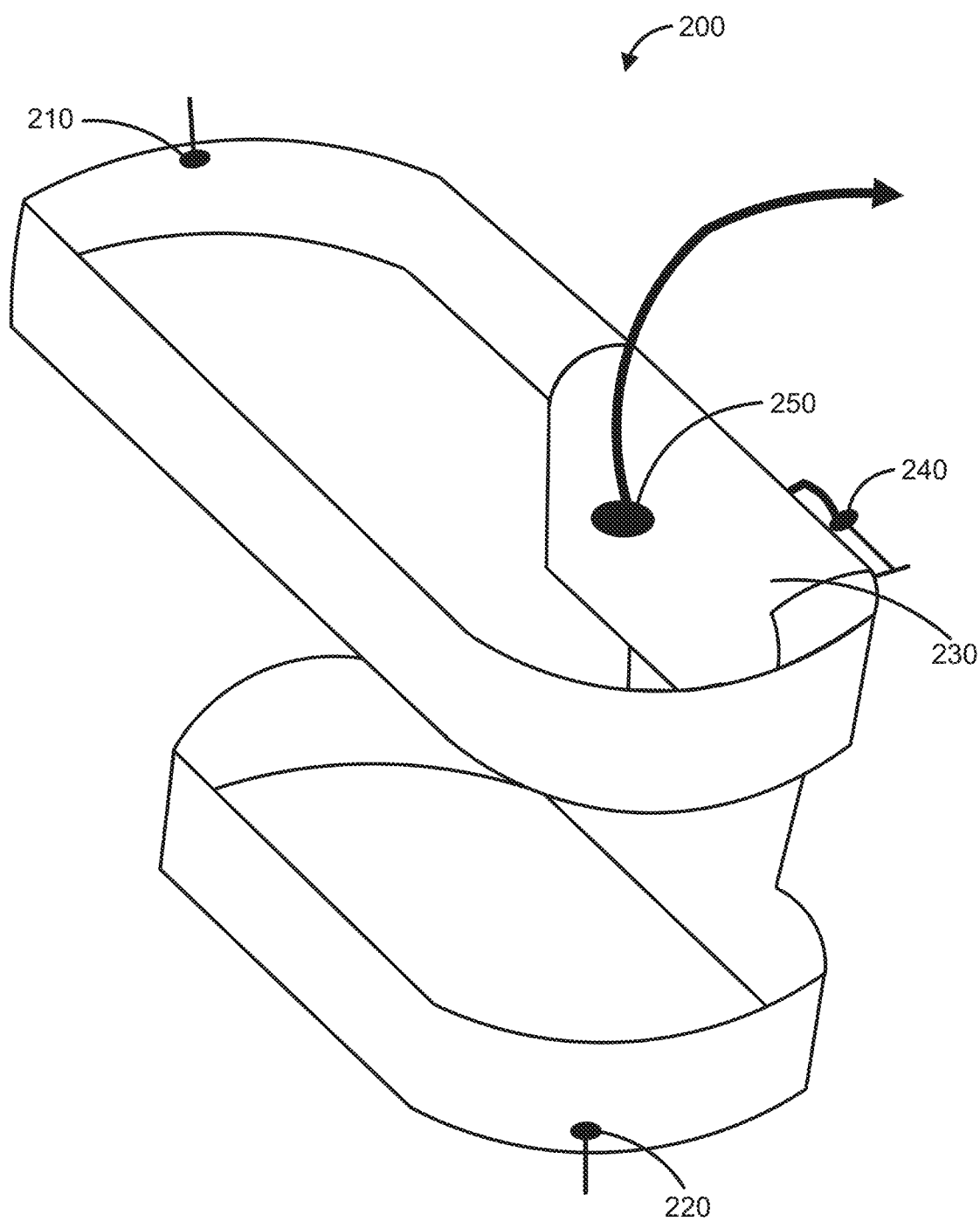
FIG. 2 illustrates an actuator device in a hip brace in accordance with various exemplary embodiments.

With reference now to FIG. 2, in accordance with an exemplary embodiment, disclosed herein is a model of an actuator device 200. In various embodiments, the actuator device comprises a strap for the hip area 210 and a strap for the thigh area 220. In various embodiments, the device also contains an inflatable fabric actuator 230 and a pressurized air inlet 240. Also illustrated is a location of a point of impact of the hip on the inflatable fabric actuator 250.

In various embodiments, the inflatable fabric actuator is pressurized using a tank, compressor or a wearable compressor. The physical device utilizes a heat-sealable double-sided TPU coated nylon fabric for creation actuator, for example sized approximately 15 cm by 15 cm. actuator. This material may be utilized because it is durable, lightweight, and capable of withstanding significant ranges in pressure; however, other suitable materials may be utilized. To integrate this actuator with the hip brace, it may be sewn into the pelvic strap utilizing a nylon fabric sheet, or via other suitable components or approaches.

In controlling the actuator, in some embodiments a force-sensitive resistor (FSR) sensor or a similar sensor is embedded into the sole of the patient's shoe on their affected leg. When the patient applies a load onto their affected leg, the sensor acts as a switch indicating a heel strike to a microprocessor unit. A set of two solenoid valves are connected in-line with each other allowing for control of inflation, deflation and holding the pressure inside of the actuator.

In operation of system 100, the gait cycle may be broken into six phases, heel strike, loading response, mid-stance, terminal stance, pre-swing, and terminal swing. An objective for the system is to pressurize the actuator during mid-stance to straighten the trunk.

In various embodiments, knowing that the pelvis is an appropriate location to provide a counter-force, a commercial hip brace that has coverage over only one half of the pelvic region may be utilized as am enclosure for the device. Having the hip brace cover only one part of the pelvis is desirable, as it allows for an actuator that could be stored therein to push only on the affected side of the hip and extend it. Further, a minimum torque that could be applied to provide the necessary support for the patient would be in a suitable range, for example about 6 N-m. An embodiment of a hip brace device containing an actuator is shown in FIG. 2.

When a hip brace is placed on the body the center of the pelvic strap was seen to be about 0.04 m above the hip joint, meaning its lever arm is about 0.04 meters. In order to provide enough force to reach the a desired torque of 6 N-m, the device may be configured to push on the hip with a suitable force, for example a force of about 150 N. The actuator designed for this hip brace may desirably fit within this pelvic strap's area, thus in some embodiments the actuator may be at most a 0.15 m by 0.15 m square bag, with an area of 0.0225 square meters. However, as the bag inflates, the area of coverage can be expected to decrease by as much as 9 times, resulting in an area of contact of about 0.0025 square meters. The maximum required pressure to have the device actuate as intended in this embodiment is approximately 68.9476 kPa, about three-fifths of atmospheric pressure. However, any suitable sizes, pressures, and configurations may be utilized, as desired.

In various embodiments, a physical device utilizes a heat-sealable double-sided TPU coated nylon fabric for creation of a 15 by 15-centimeter actuator. This material was used because it is durable, lightweight, and capable of withstanding significant ranges in pressure. To integrate this actuator with the hip brace, it was sewn into the pelvic strap utilizing a nylon fabric sheet. This allows for the device to expand inside of a constrained space, allowing force to propel primarily in the direction of the hips while also maintaining a degree of comfort for the user. However, any suitable coupling mechanisms may be utilized.

Figure 3:
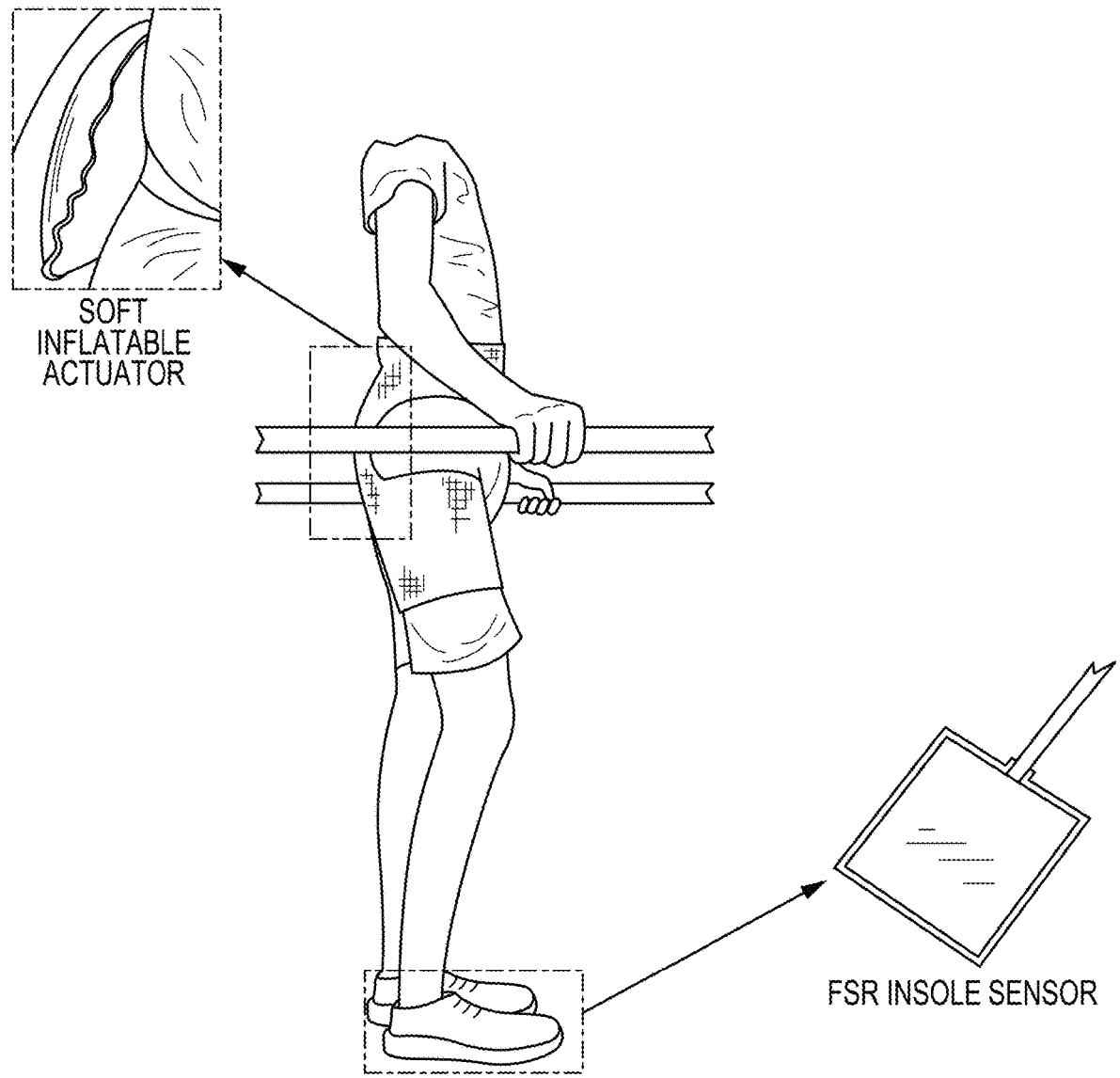
FIG. 3 illustrates an example of an individual wearing a hip brace that contains a soft inflatable actuator and an FSR insole sensor in accordance with various exemplary embodiments.

In controlling the actuator in various embodiments, a force-sensitive resistor (FSR) sensor is embedded into the sole of the patient's shoe on their affected leg. When the patient applies a load onto their affected leg, the sensor acts as a switch indicating to a controller, for example an Arduino Duo development board, to activate two solenoid valves. The solenoid valves are connected in-line with each other allowing for control over inflation, deflation and holding of the pressure inside of the actuator. The rate by which inflation and deflation occurs is regulated by an on-board pressure sensor and a high isolation voltage SSOP photocoupler. The pressure sensor provides feedback to the solenoid valves by restricting the flow of air beyond safe levels for the actuator and providing only what is desirable to operate the system. An individual wearing a hip brace that contains a soft inflatable actuator and an FSR insole sensor in accordance with various embodiments is shown in FIG. 3.

Figure 4B:
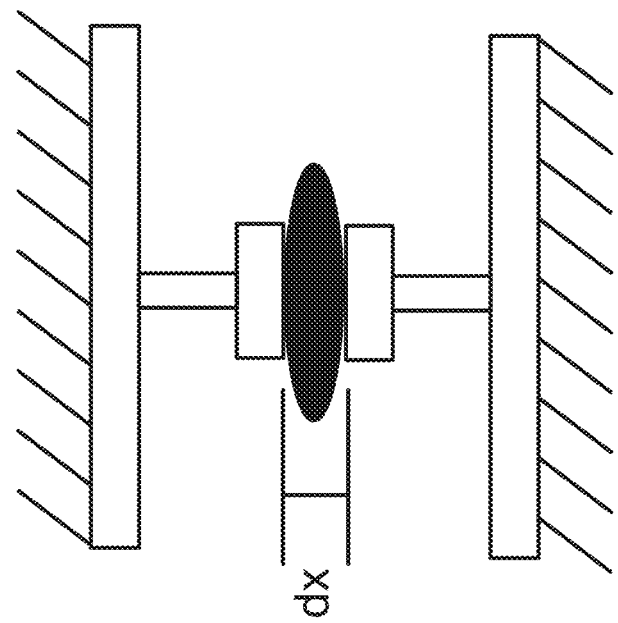
FIGS. 4A and 4B depict an experimental setup of actuator testing under UTM, in accordance with various exemplary embodiments.
Figure 4A:
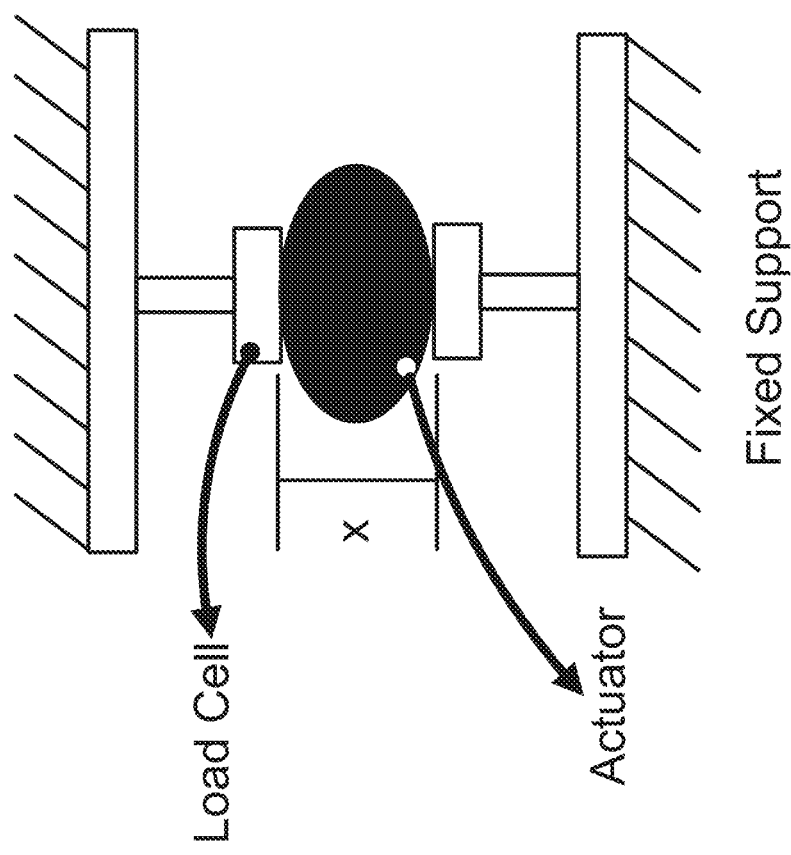

In order to validate performance of exemplary devices, three tests, including actuator, torque and walking tests may be conducted. The actuator test was carried out to measure the force generated. The torque test was carried out to check the applied assistance and the walking test was carried out to analyze the effect of the device on the muscles. FIGS. 4A-4B illustrate an experimental setup showing an actuator exerting force at full extension (FIG. 4A) and at restricted extension (FIG. 4B).

Utilizing a universal testing machine (UTM), the actuator was fastened to the bottom plate of the machine and allowed to inflate and push on a force plate directly above it. In one embodiment, actuator force output was measured to be 267 N at 103.42 kPa pressure for initial calculations using the UTM. The force plate was fixed at different depths ranging from 0.040 to 0.060 meters, and as the actuator inflated, the device presses against the force plate, providing readings of the force the plate experiences from the device.

Figure 5:
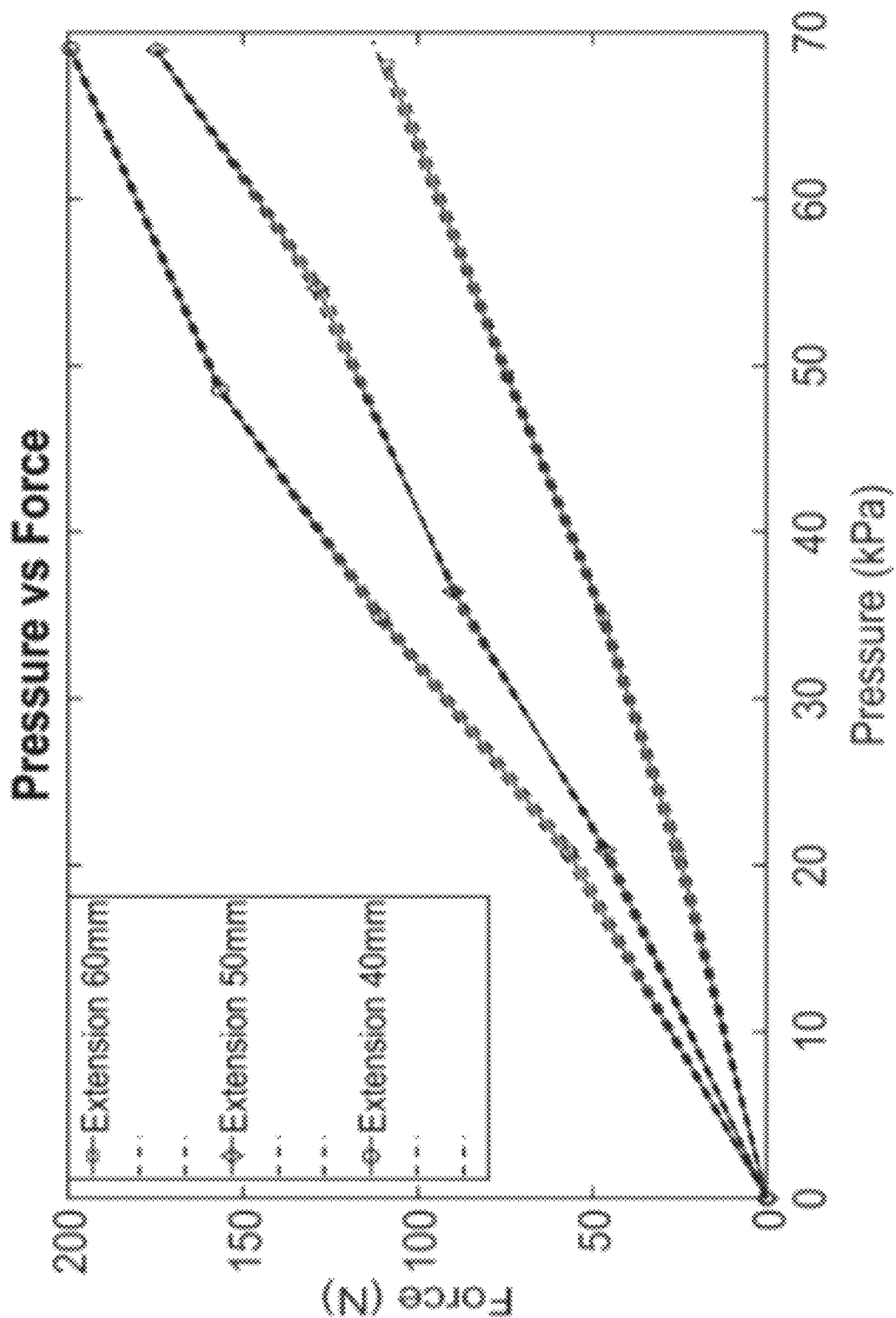
FIG. 5 depicts a graph of data for force vs. pressure at the fixed force plate positions of 40, 50, and 60 mm in accordance with various exemplary embodiments.

FIG. 5 demonstrates that at greater allowance for expansion of the device, the less force it is able to exert in the direction of its inflation. The greatest force exerted was found at an expansion allowance of 0.040 m with the device set at 68.95 kPa of pressure. This is based on the formula, $p1V1=p2V2$. However, device size, inflation pressure, and so forth may be selected to provide a desired amount of force over a desired expansion allowance.

Given the foregoing, it is desirable to utilize device 100 in a constrained environment in order to exert its maximum force. Thus, by installing the device inside of the hip brace, the actuator is constrained to the body and able to firmly push on the hip of the patient.

Figure 6:
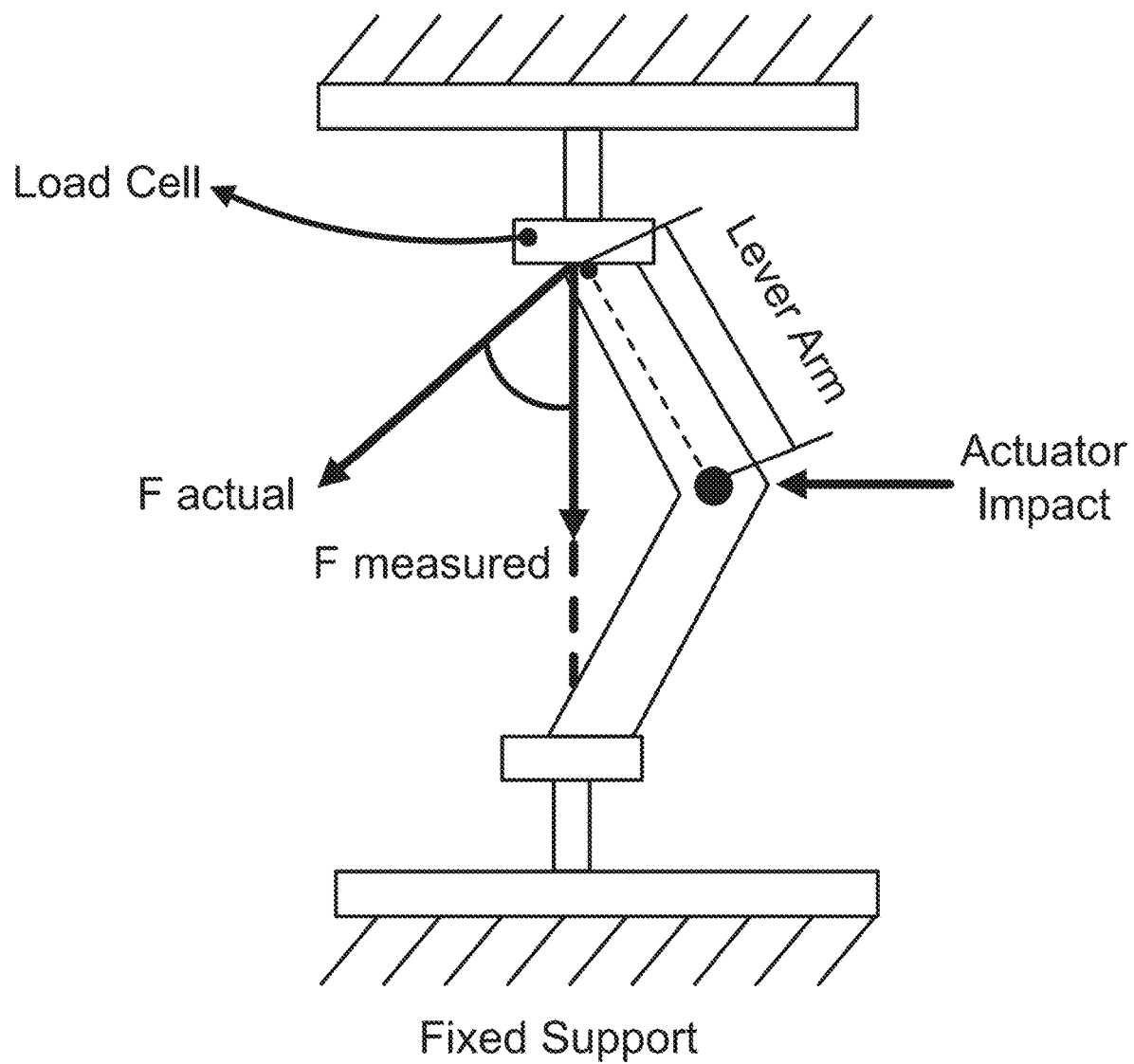
FIG. 6 depicts an experimental setup of a bio-inspired hip joint for torque analysis of an actuator in accordance with various exemplary embodiments.

Utilizing the universal testing machine, a bio-inspired hip joint apparatus was attached to the top and bottom plates at fixed angles to provide information of the torques at different angles using fixed pressures. The angle measurements were chosen between 10 and 15 degrees to resemble similar angular deflections identified in patients characterized with hemiparesis. The top plate of the UTM had a load cell, and was fixed to allow for force readings to be had on the output from device as it pushed on the joint of the apparatus (See FIG. 6). The data collected can be seen in the graph shown in FIG. 7.

Figure 7:
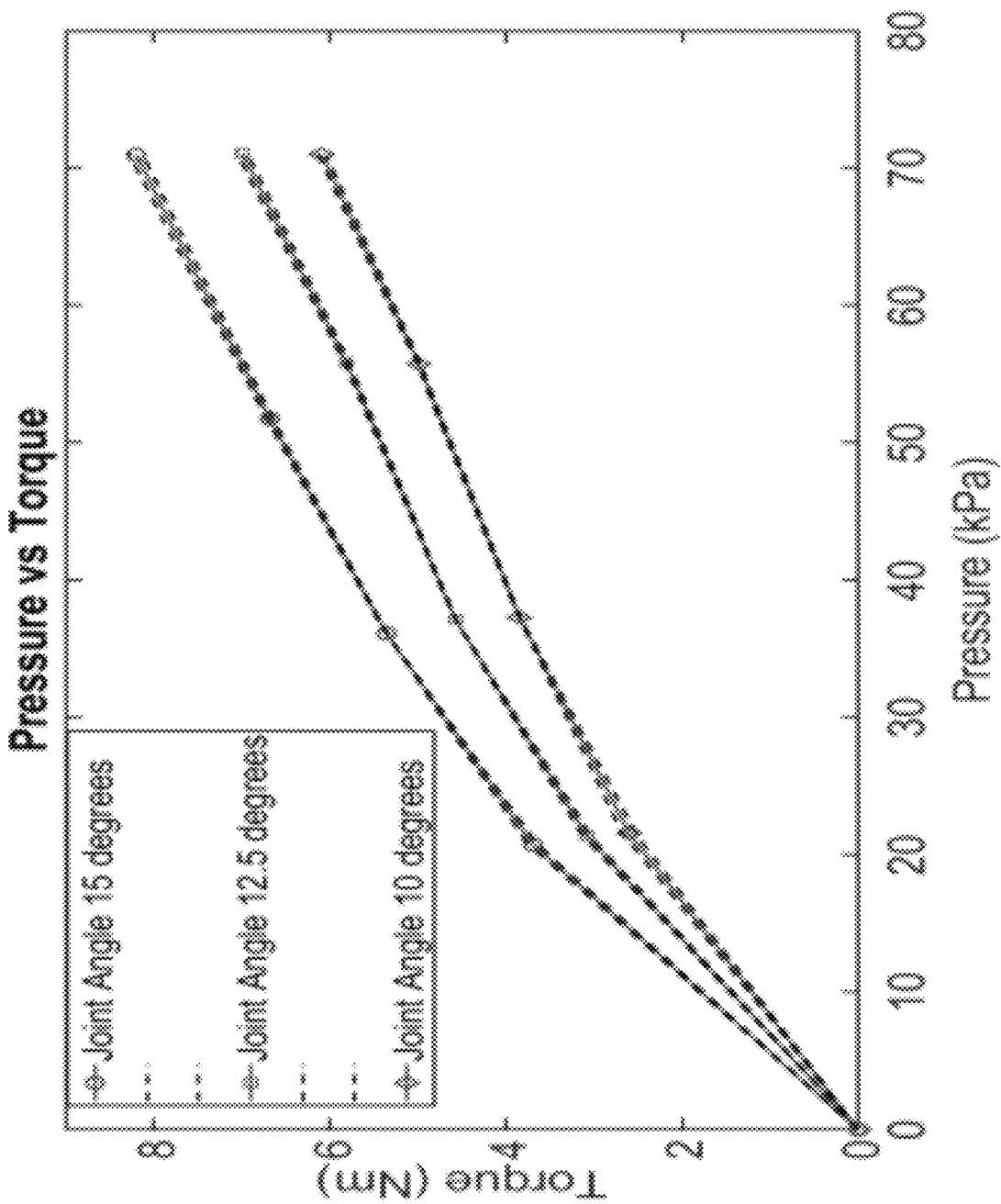
FIG. 7 depicts graph of data for torque vs. pressure at the joint angles of 15, 12.5, and 10 degrees in accordance with various exemplary embodiments.

From FIG. 7, it shows that as the joint angle of the hip increases, the torque increases almost linearly. It also demonstrates that at greater pressures, the device is able to exert greater torques. This data also demonstrates that the device is able to satisfy the about 6 N-m desired for a 30% support from the device at pressures around 60 kPa.

In testing the function of exemplary devices on a person, walking trials were done on an instrumented treadmill with force plates surrounded with motion capture cameras. While stitched inside of the hip brace, the actuator inflates until the cloth constricted its motion in both directions, after which, the actuator would begin propelling the hip forward. The user was then asked to walk at a pace that allowed for them to maintain their position on the treadmill to mimic the walking speed of a stroke affected patient (0.4 m/s).

To gather data from this trial, pearl reflective markers were placed on the tester in order to capture the motion from their feet up to their hip. In addition to this, Trigno Wireless EMG sensors were used in order to gather data on the muscle activation during the motion for the iliopsoas group, and the gluteus medius and maximus. These three muscles drive majority of locomotion for flexion and extension of the hip joint. The locations for these sensors are depicted in FIG. 8.

Figure 8:
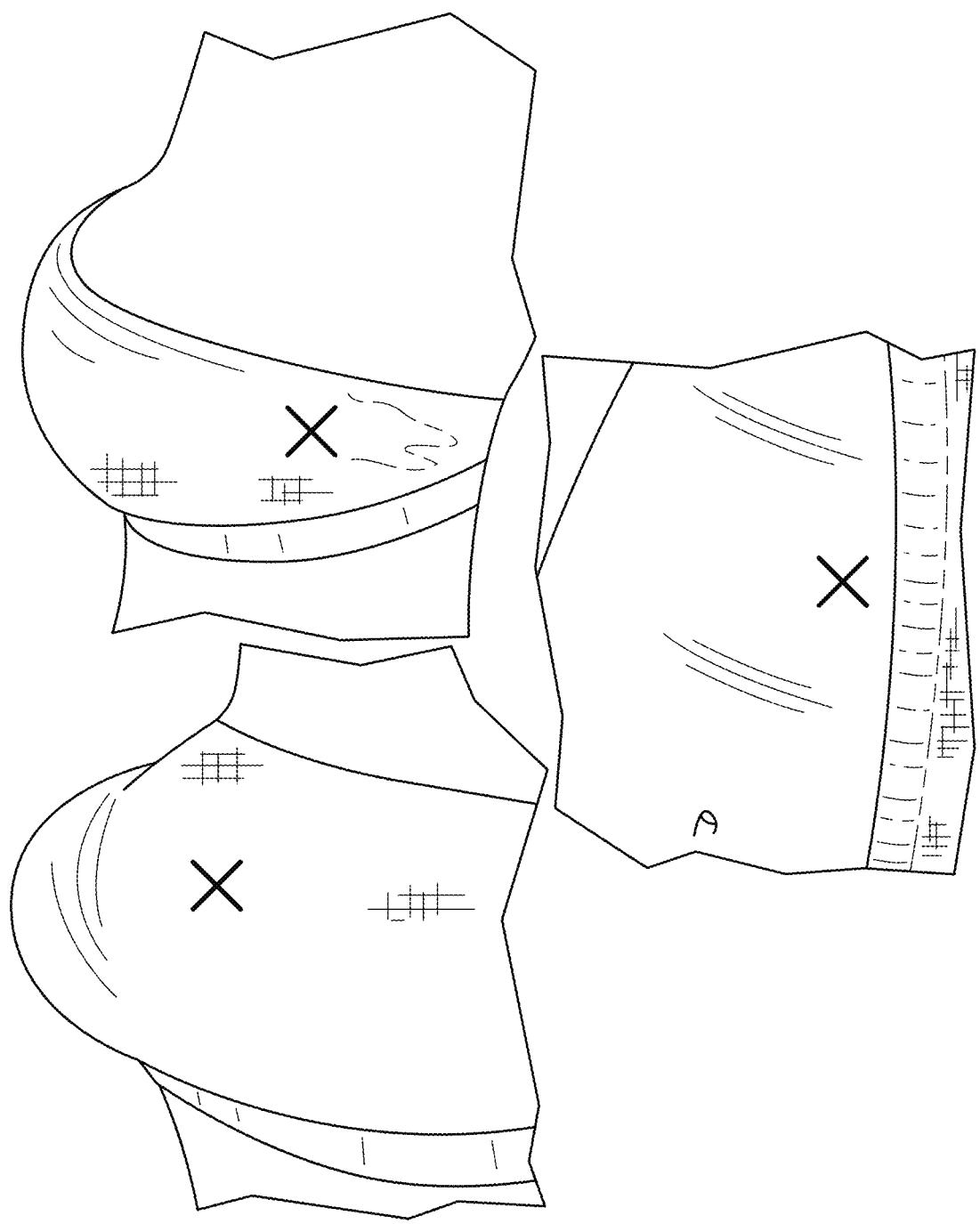
FIG. 8 depicts EMG placement locations for the gluteus maximus (top, left) and gluteus medius (top, right) marked by an "X", and EMG placement for the iliopsoas (bottom) is the lower electrode, also marked by an "X", all in accordance with various exemplary embodiments.
Figure 9A:
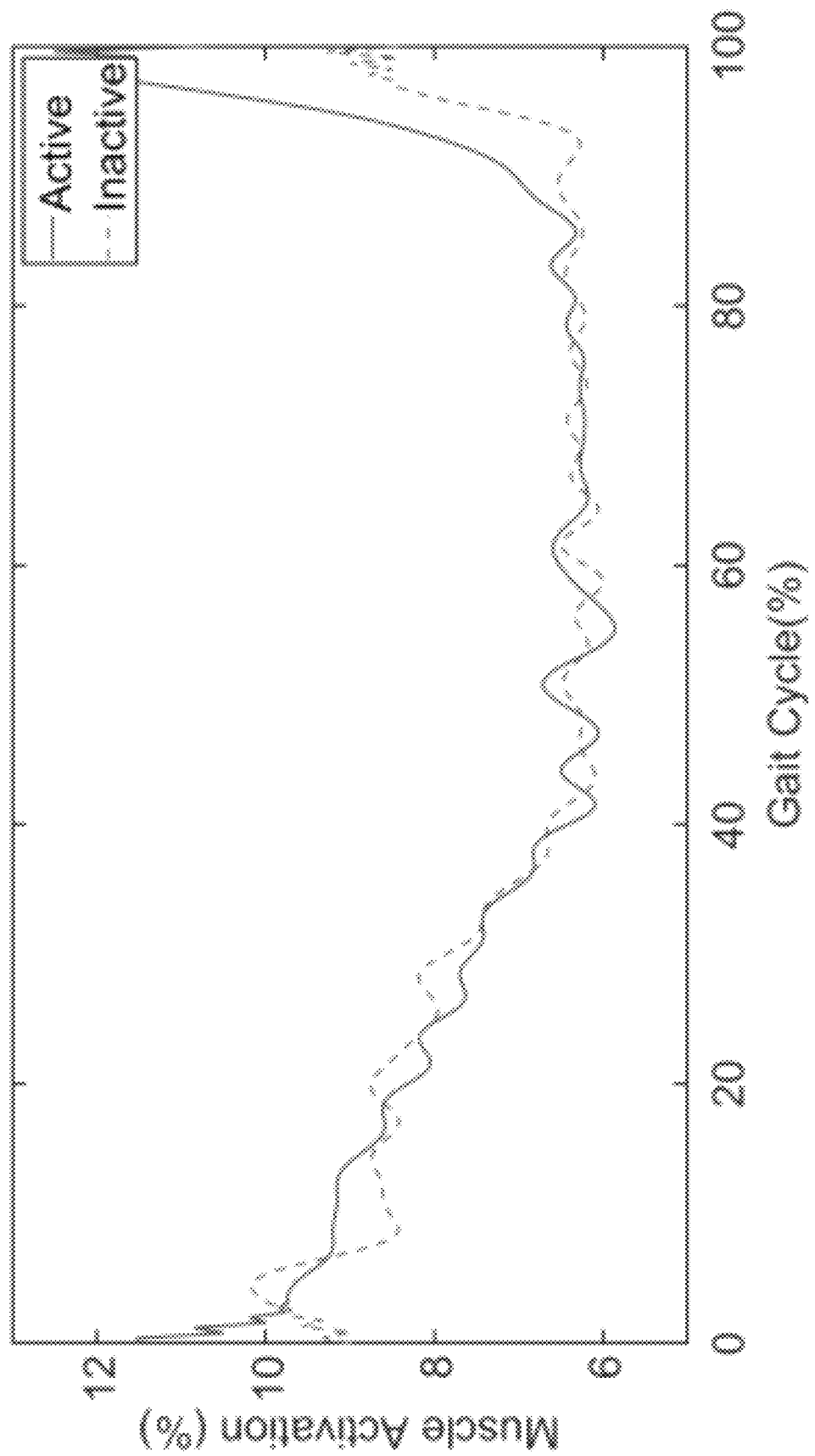
FIGS. 9A-9F depict EMG results demonstrating the sensor readings when the actuation is active (solid line), and when the actuation is inactive (dotted line), in accordance with various exemplary embodiments.
Figure 9B:
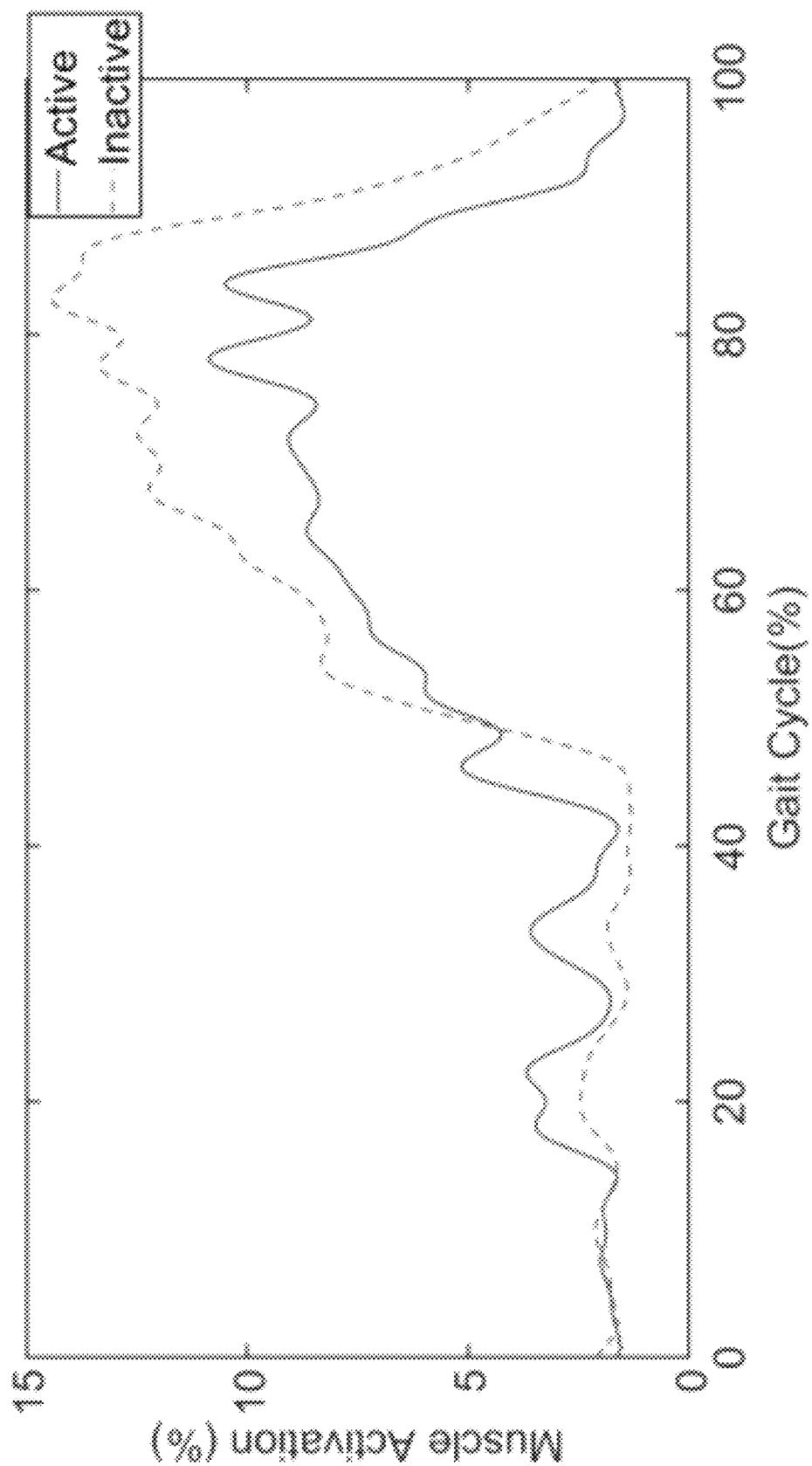
Figure 9C:
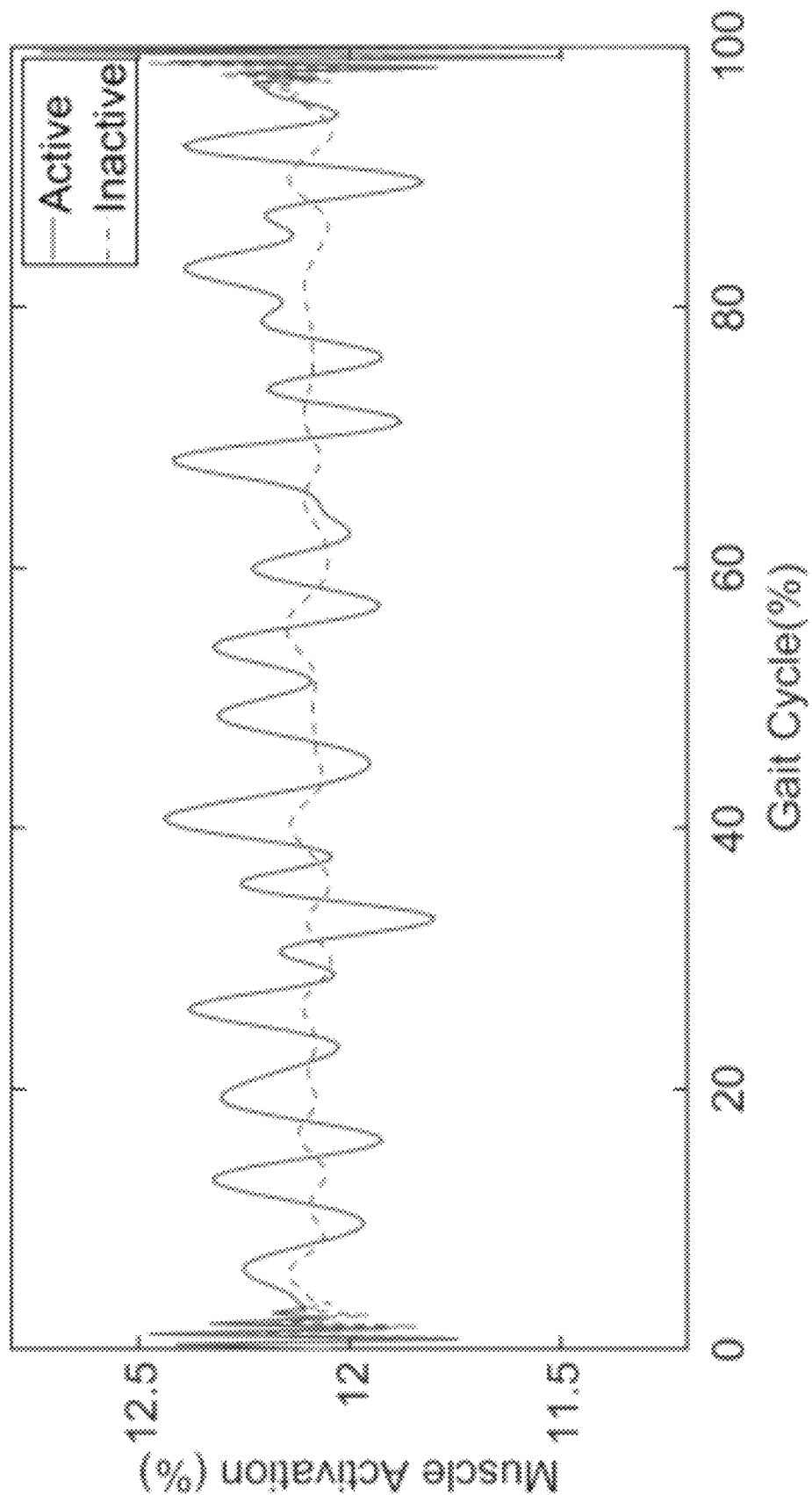
Figure 9D:
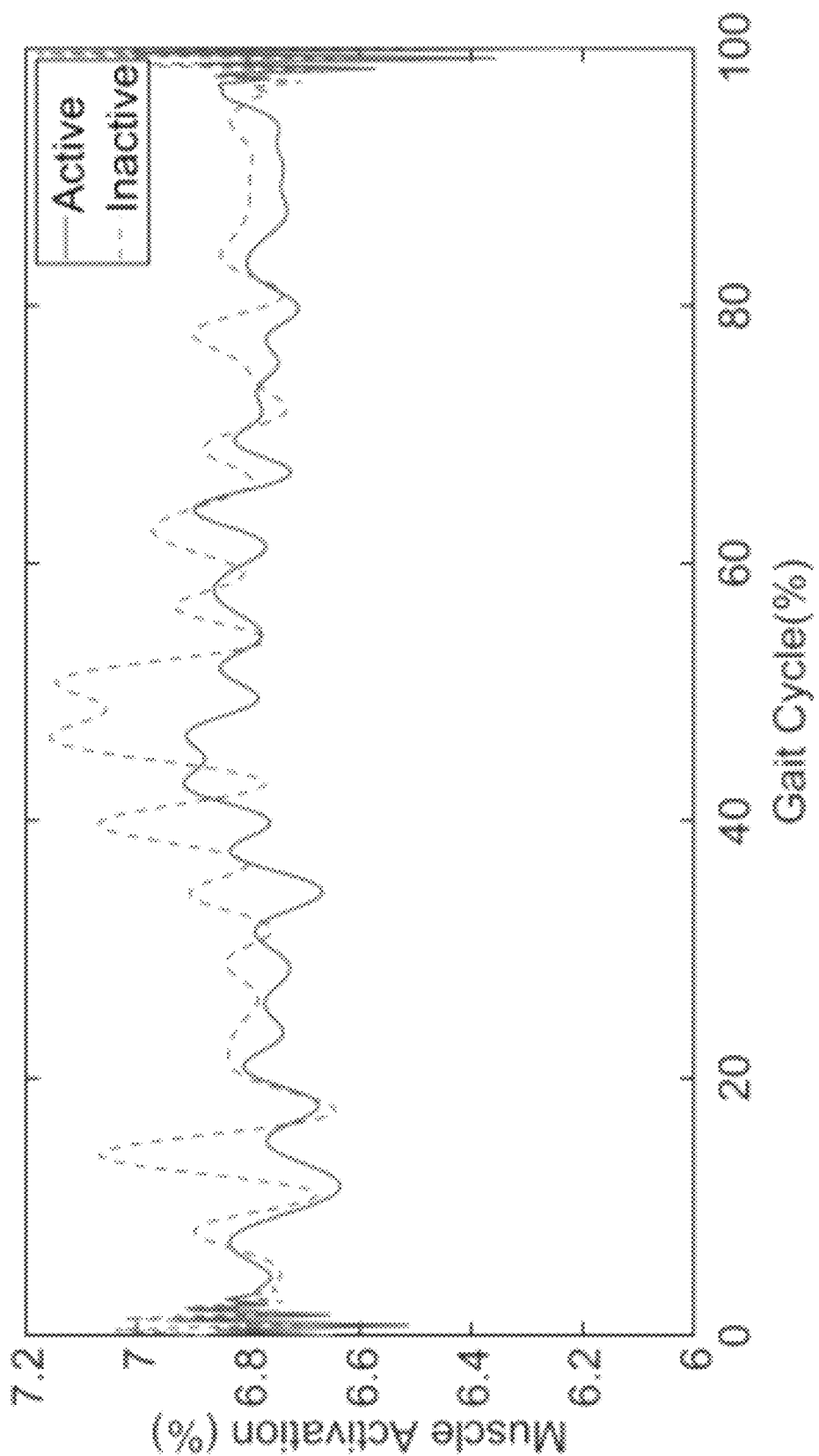
Figure 9E:
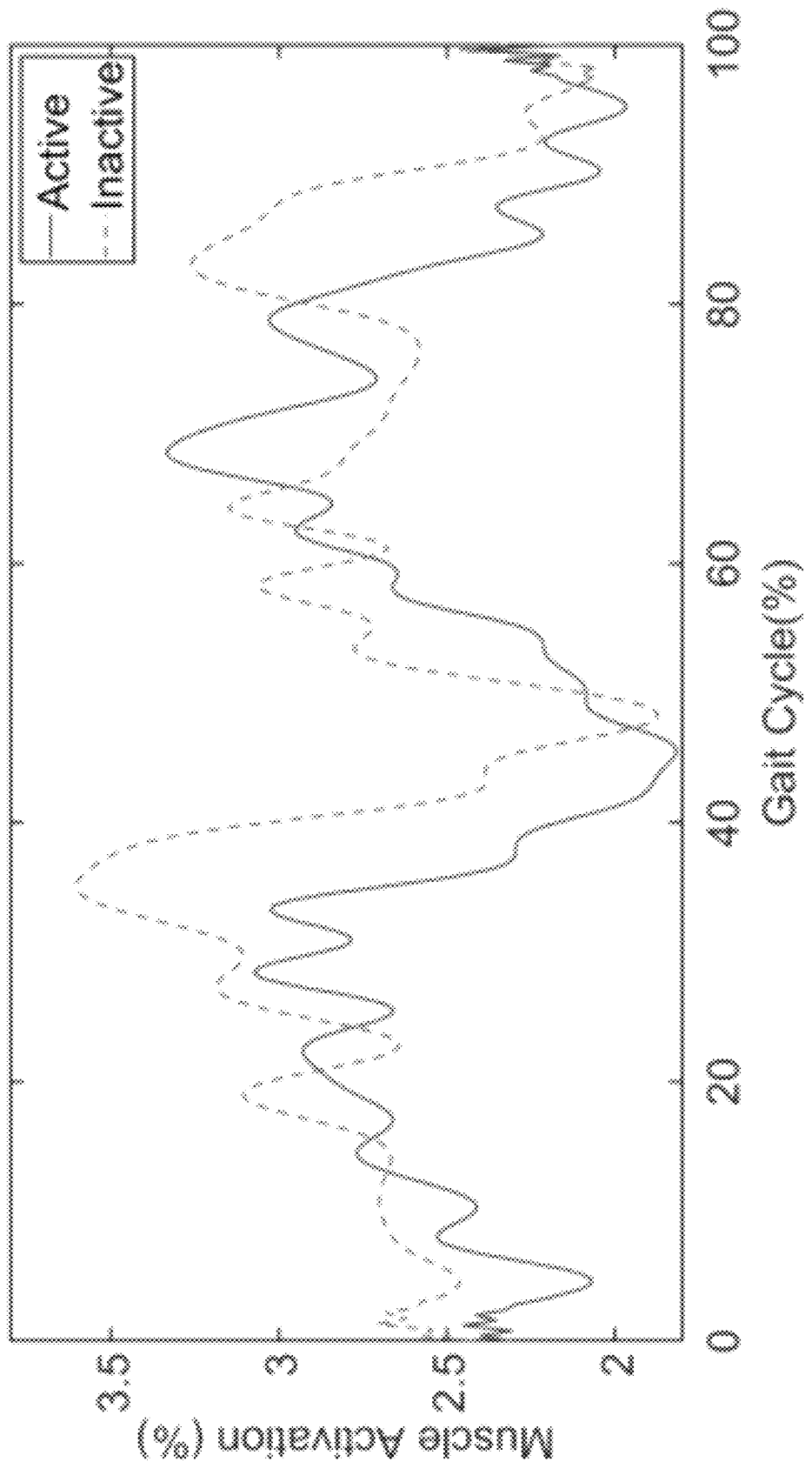
Figure 9F:
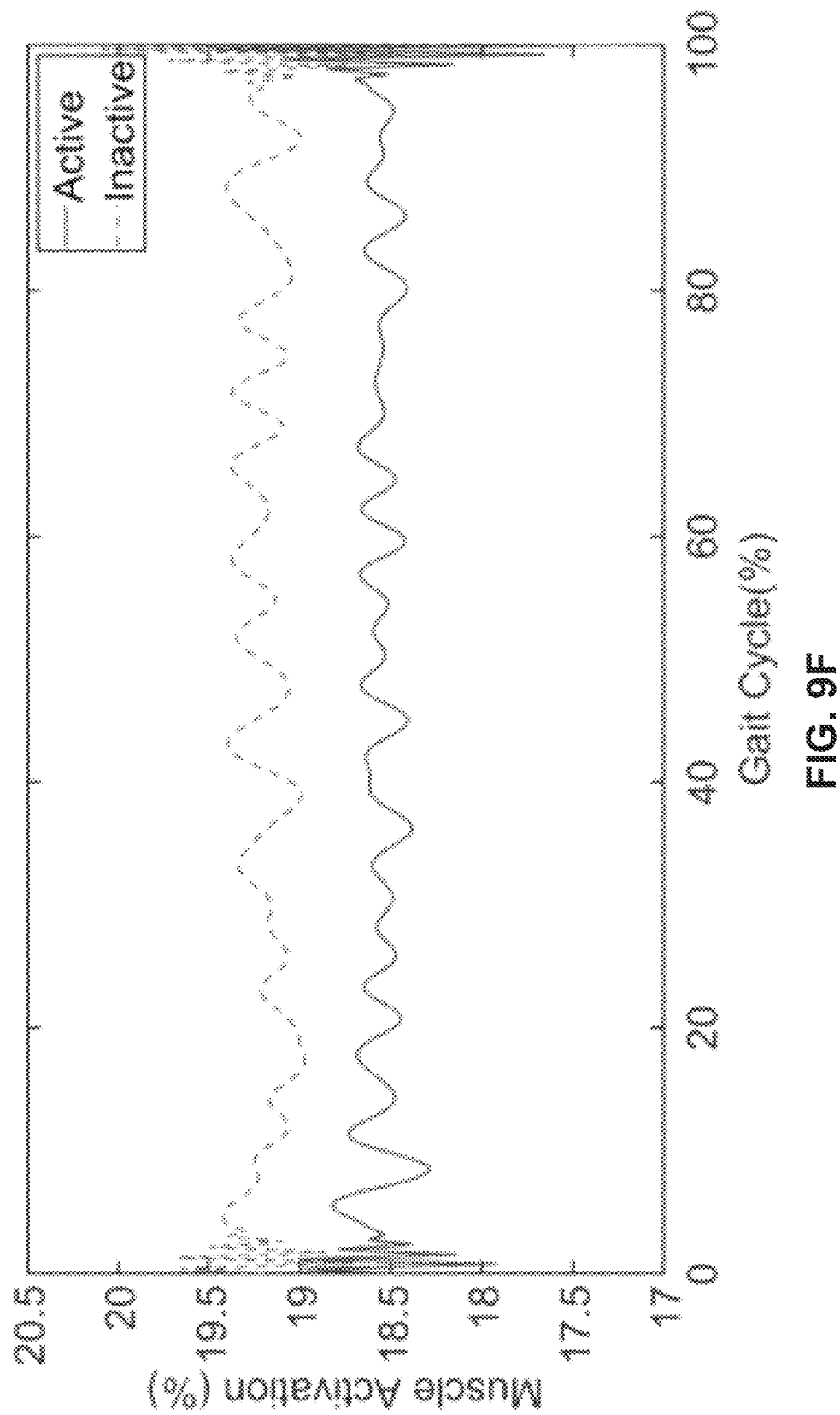

FIG. 8 shows the placement of EMGs on the muscles associated with hip extension according to ISEK standards. Because the device is made to support muscle contractions in the extensors to realign the hips, readings when the device is active should appear less than when it is inactive. Exemplary data collected from the sensors are shown in FIGS. 9A-9F.

In some embodiments, three trials are performed on a tester: one without device 100, one with the device in an inactive state, and another with the device in an active state. EMG data collected by these tests compares the effect of the device on the muscle activation during a gait cycle. About 40 gait cycles are averaged for all three testing conditions for the gluteus maximus, gluteus medius and the iliopsoas muscle group and plotted with their mean as shown in FIGS. 9A-9F. As seen, muscle activation is decreased by about 5% at the most for the gluteus medius, about 1% for the iliopsoas, and less than 0.5% for the gluteus maximus during testing with the device active. The findings are compatible with the documentation found on EMG data in regard to these three muscle groups. The fact that all of the muscles demonstrate a decrease in activity during activation of the device demonstrates the effectiveness it has in providing the support intended.

In addition, a test was carried out to quantify whether the range of motion is affected by the device. Reflective bead markers were placed on the legs of the tester from their hip to their shoe to allow for data capture on the effects of the device on extending the hip of the user. With this experimental setup, range of motion with and without the device was studied. The graphs in FIGS. 10A and 10B show both sides of the hip as the device is activated and deactivated during the gait of the tester.

Figure 10A:
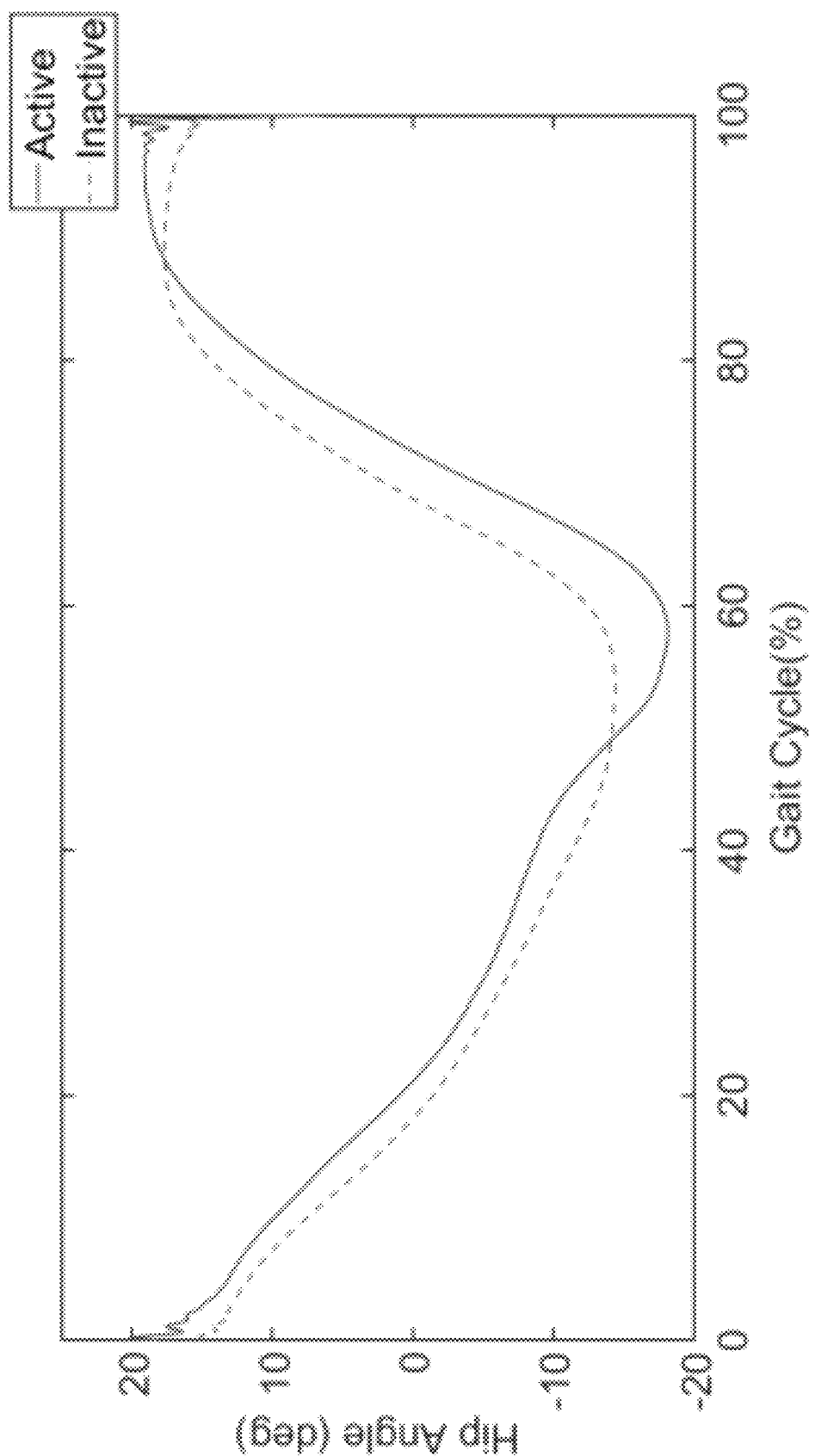
FIGS. 10A-10B depict hip range of motion of a patient for the side of the hip, in accordance with various exemplary embodiments.
Figure 10B:
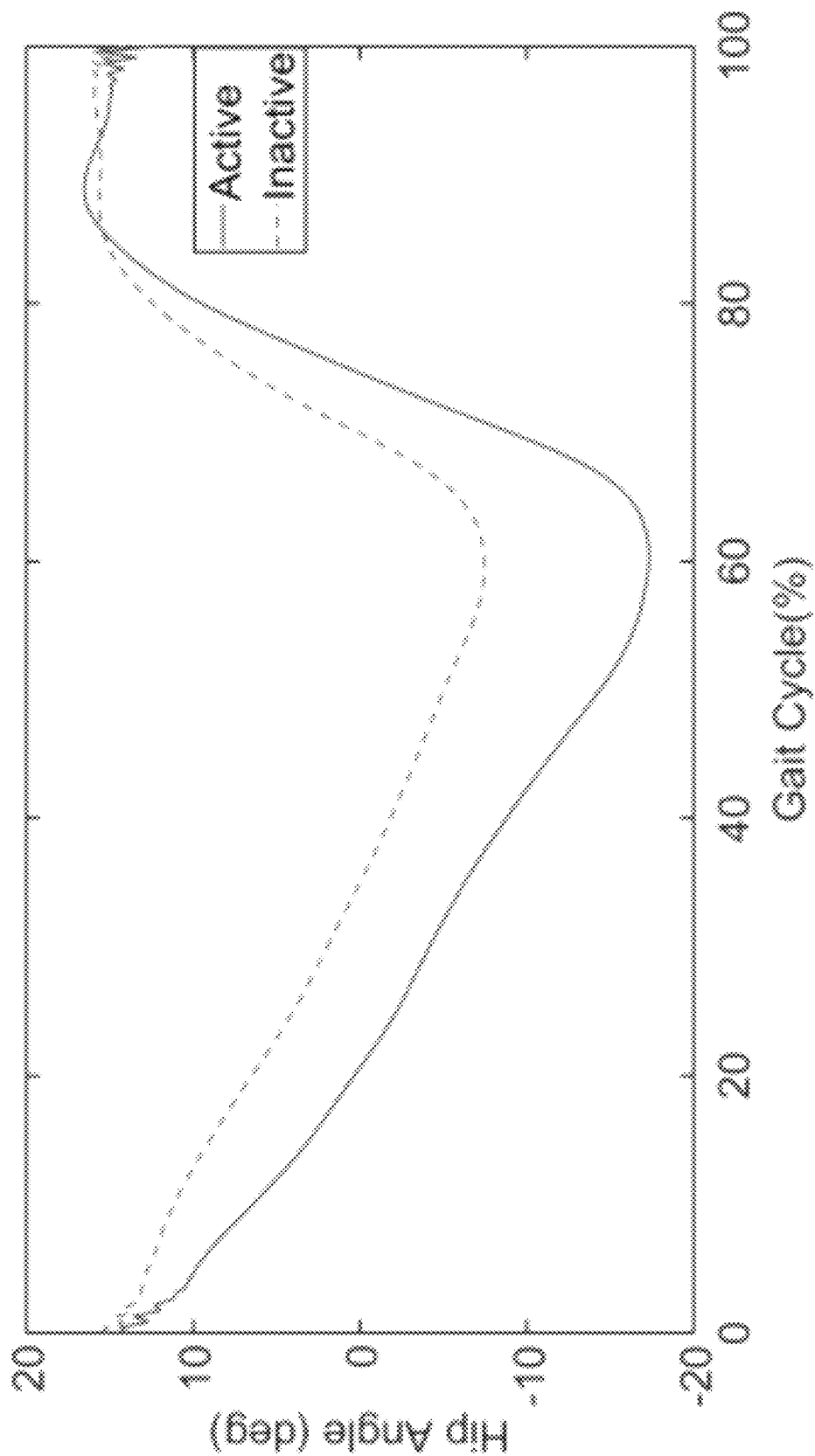

FIGS. 10A and 10B show the total hip angle prior to wearing the device is 22±2°. The range of motion while wearing the device is 32±2°. This demonstrates a 10-degree extension in the range of motion of the hips found in the 45-60% gait cycle range. The data also verifies that the device does not obstruct 70% of the range of motion, again speaking to the efficacy of the device.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A soft wearable robotic device, comprising:
   an inflatable actuator located on only a gluteus muscle group of a wearer when inserted inside a compressive hip brace comprising a lever arm having a length of approximately 0.04 meters;
   a force sensitive resistor (FSR) embedded in a sole of a shoe and configured to detect a heel strike on the shoe; and
   control components configured to activate the inflatable actuator to inflate to a pressure of approximately three-fifths of atmospheric pressure, thereby providing a perpendicular force of approximately 150 Newtons to only the gluteus muscle group responsive to the FSR detecting the heel strike, thereby indicating that the wearer is loading on an affected limb, wherein:
      the control components comprise two interconnected solenoid valves, a pressure sensor, and a high isolation SSOP photocoupler; and
      the perpendicular force propels a hip of the wearer forward with a torque of approximately 6 Newton-meters as the wearer is loading on the affected limb.

2. The soft wearable robotic device of claim 1, further comprising a force-sensitive resistor (FSR) sensor configured to detect changes in force being applied to the affected limb and configured to communicate the detected changes in the force to the two interconnected solenoid valves.

3. The soft wearable robotic device of claim 1, wherein:
   the inflatable actuator comprises a plastic pouch inside of a layer of fabric;
   the inflatable actuator is pressurized using a tank, compressor or a wearable compressor;
   the inflatable actuator is pressurized during a mid-stance phase of a gait cycle; and
   the soft wearable robotic device does not obstruct at least 70 percent of a range of motion of a hip joint associated with the soft wearable robotic device.

4. The soft wearable robotic device of claim 1, wherein the pressure sensor provides feedback to the two interconnected solenoid valves to prevent the inflatable actuator from exerting an injurious force on the gluteus muscle group.

5. The soft wearable robotic device of claim 1, wherein the perpendicular force causes an increase of at least 5% to a range of motion of the hip as compared to a range of motion of the hip without the soft wearable robotic device.

6. The soft wearable robotic device of claim 1, wherein the perpendicular force causes a decrease of at most 5% to activation of the gluteus muscle group as compared to activation of the gluteus muscle group without the soft wearable robotic device.

7. A device, comprising:
a hip brace comprising a pelvic strap, a thigh strap, and a lever arm having a length of approximately 0.04 meters, wherein the hip brace is configured to cover one half of a pelvic region of a patient;
an inflatable fabric actuator located in the pelvic strap and only on a gluteus muscle group, the inflatable fabric actuator comprising a pressurized air inlet;
a force sensitive resistor (FSR) embedded in a sole of a shoe and configured to detect a heel strike on the shoe; and
two interconnected solenoid control components comprising valves, a pressure sensor, and a high isolation voltage SSOP photocoupler;
wherein the two interconnected solenoid control components comprising the valves, the pressure sensor, and the high isolation voltage SSOP photocoupler are configured to control inflation and deflation of the inflatable fabric actuator in response to the FSR detecting the heel strike, and
wherein, when inflated to a pressure of approximately three-fifths of atmospheric pressure, the inflatable fabric actuator applies a perpendicular force of approximately 150 Newtons to only the gluteus muscle group, thereby propelling a hip of a wearer of the device forward with a torque of approximately 6 Newton-meters.

8. The device of claim 7, wherein the inflatable fabric actuator comprises an area of no more than 0.0225 square meters, when the inflatable fabric actuator is not inflated.

9. The device of claim 7, wherein the inflatable fabric actuator comprises an area of contact on the pelvic strap of no more than 0.0025 square meters, when the inflatable fabric actuator is inflated.

10. The device of claim 7, wherein the inflatable fabric actuator is coated with thermoplastic polyurethane.

11. The device of claim 7, further comprising a compressor configured to pressurize the inflatable fabric actuator.

12. The device of claim 7, wherein:
the inflatable fabric actuator comprises a plastic pouch inside of a layer of fabric;
the inflatable fabric actuator is pressurized using a tank, compressor or a wearable compressor;
the inflatable fabric actuator is pressurized during a mid-stance phase of a gait cycle; and
the device does not obstruct at least 70 percent of a range of motion of a hip joint associated with the device.

13. A system, comprising:
an inflatable fabric actuator configured to be placed only on a gluteus muscle group of a patient;
a hip brace coupled to the inflatable fabric actuator and comprising a lever arm having a length of approximately 0.04 meters; and
a force sensitive resistor (FSR) embedded in a sole of a shoe and configured to detect a heel strike on the shoe,
wherein, when inflated to a pressure of approximately three-fifths of atmospheric pressure in response to the FSR detecting the heel strike, thereby indicating a load being applied to a leg, the inflatable fabric actuator is capable of applying a force of approximately 150 Newtons to only the gluteus muscle group of the patient, thereby resulting in extension and forward movement of a hip of the patient with a torque of approximately 6 Newton-meters and straightening of a body of the patient, and
wherein the inflatable fabric actuator comprises two interconnected solenoid valves, a pressure sensor, and a high isolation voltage SSOP photocoupler.

14. The system of claim 13, wherein the hip brace comprises:
a first strap configured to secure the inflatable fabric actuator against the gluteus muscle group of the patient; and
a second strap configured to secure the inflatable fabric actuator against the leg of the patient.

15. The system of claim 13, wherein the heel strike results in the pressure changes in the inflatable fabric actuator and pressurizes the inflatable fabric actuator during mid-stance of a gait cycle resulting in straightening of the body of the patient.

16. The system of claim 13, wherein:
the inflatable fabric actuator comprises a plastic pouch inside of a layer of fabric;
the inflatable fabric actuator is pressurized using a tank, compressor or a wearable compressor;
the inflatable fabric actuator is pressurized during a mid-stance phase of a gait cycle; and
the system does not obstruct at least 70 percent of a range of motion of a hip joint associated with the system.

* * * * *